United States Patent [19]
Colman et al.

[11] Patent Number: 5,665,065
[45] Date of Patent: Sep. 9, 1997

[54] MEDICATION INFUSION DEVICE WITH BLOOD GLUCOSE DATA INPUT

[75] Inventors: Fredric C. Colman, Granada Hills; Peter C. Lord, Santa Clarita, both of Calif.

[73] Assignee: MiniMed Inc., Sylmar, Calif.

[21] Appl. No.: 452,406

[22] Filed: May 26, 1995

[51] Int. Cl.[6] .................... A61M 35/00; A61M 37/00
[52] U.S. Cl. .................. 604/66; 604/50; 604/65; 604/67; 604/93; 604/131
[58] Field of Search ................ 604/50, 51, 52, 604/53, 65, 66, 93, 95, 131, 132

[56] References Cited

U.S. PATENT DOCUMENTS

| | | | |
|---|---|---|---|
| 3,837,339 | 9/1974 | Aisenberg et al. | 128/213 |
| 4,633,878 | 1/1987 | Bombardieri | 604/31 |
| 4,871,351 | 10/1989 | Feingold | 604/66 |
| 5,101,814 | 4/1992 | Palti | 604/31 |
| 5,104,374 | 4/1992 | Bishko et al. | 604/65 X |
| 5,165,407 | 11/1992 | Wilson et al. | 128/635 |
| 5,372,133 | 12/1994 | Hogen Esch | 128/631 |
| 5,376,070 | 12/1994 | Purvis et al. | 604/31 |
| 5,383,865 | 1/1995 | Michel | 604/232 |
| 5,391,157 | 2/1995 | Harris et al. | 604/208 |
| 5,497,772 | 3/1996 | Schulman et al. | 604/66 X |

FOREIGN PATENT DOCUMENTS 0554 995A1  8/1993  European Pat. Off. .

OTHER PUBLICATIONS

Therapeutic Strategies in the Patient with Uncontrolled Diabetes Mellitus—Davidson May 20, 1988.

*Primary Examiner*—Sam Rimell
*Assistant Examiner*—Robert V. Racunas
*Attorney, Agent, or Firm*—Kelly Bauersfeld Lowry & Kelley, LLP

[57] ABSTRACT

A medication infusion device such as a programmable infusion pump includes data input regarding a selected patient parameter such as a current blood glucose reading. The infusion device includes a controller responsive to this data input to develop a medication delivery protocol which can be implemented automatically, recommended via a display for subsequent approval or rejection upon manipulation of control switches, or otherwise overridden in favor of a different medication delivery protocol.

21 Claims, 2 Drawing Sheets

MEDICATION INFUSION DEVICE WITH BLOOD GLUCOSE DATA INPUT

BACKGROUND OF THE INVENTION

This invention relates generally to improvements in medication infusion devices for use in delivering a selected medication to a patient. More specifically, this invention relates to a medication infusion device such as a programmable infusion pump or similar apparatus adapted for response to a parameter indicative of patient condition, such as a current blood glucose reading.

Infusion pump devices and systems are generally known in the medical arts, for use in delivering or dispensing a prescribed medication to a patient. In one form, such devices comprise a relatively compact pump housing adapted to receive a syringe carrying a prescribed medication such as insulin for administration to a patient through infusion tubing and an associated catheter or the like. The infusion pump operates a small drive motor connected to a syringe piston plunger to administer the medication to the patient.

Programmable control means are normally provided for operating the pump drive motor continuously, or at periodic intervals, to obtain a closely controlled and accurate delivery of medication over an extended time period. Such infusion pumps are utilized to administer insulin and other medications, with an exemplary pump construction being shown and described in U.S. Pat. Nos. 4,562,751; 4,678,408; and 4,685,903.

A typical programmable infusion pump includes a plurality of externally accessible control switches or buttons which can be manipulated in relation to a visual display to program the pump in accordance with patient medication requirements. Initial pump programming is normally performed by the patient's physician or by other medical personnel. However, particularly in the case of infusion pumps used to administer insulin to diabetic patients, the control buttons and related pump control circuitry are often designed to accommodate at least some patient intervention to vary medication delivery times and doses in accordance with anticipated patient requirements.

One alternative medication infusion device comprises a compact syringe-type implement constructed to resemble a fountain pen or the like, and thus adapted to be carried easily and conveniently by the patient. See, for example, U.S. Pat. Nos. 5,383,865 and 5,391,157, and European Patent Publication 0,554,995. Such pen-like implements include a rotatable dial or knob for retracting a syringe plunger through a predetermined stroke, with a visual display providing an indication of the medication units or volume to be delivered upon subsequent manual advancement of the plunger. The patient can thus set the implement to deliver a desired dosage, and then press the plunger to deliver the medication. The medication dosage and frequency are, of course, developed according to a dispensing protocol to meet the needs of each specific patient.

In recent years, there has been considerable interest in the development of improved medication infusion devices which can be used to deliver medication to the patient in accordance with current or actual patient requirements, as distinguished from anticipated medication requirements. In this regard, blood chemistry readings can provide current information regarding important patient condition parameters that can affect current or actual patient medication requirements. For example, blood glucose readings represent key data that can be used to determine current insulin requirements of a diabetic patient. Extensive research is ongoing with respect to the development of improved and reliable glucose sensors, for example, as described in U.S. Pat. Nos. 4,650,547; 4,671,288; 4,781,798; 4,703,756; and 4,890,620. Similarly, a variety of systems have been proposed for use of a glucose sensor to automatically alter the operation of a medication infusion pump in response to current patient requirements, as described, for example, in U.S. Pat. Nos. 4,633,878; 3,837,339; 5,101,814; and 5,372,133.

While automatic control of an infusion device for insulin or other medication appears to be a desirable approach for some patients, diabetic patients often need more flexibility in their individual medication delivery protocols in order to accommodate a normal daily living schedule. That is, while a current blood glucose reading is an important factor in determining medication requirements, variable daily activity such as changing eating schedules, exercising schedules, etc., should be taken into account in determining the actual dosage and timing of medication delivery to each individual patient.

There exists, therefore, a significant need for further improvements in medication infusion devices of the type adapted for response to a current patient condition parameter, such as a current blood glucose reading, wherein actual dispensing of medication to the patient represents a balanced response which considers the monitored parameter in addition to current subjective patient activity factors. The present invention fulfills these needs and provides further related advantages.

SUMMARY OF THE INVENTION

In accordance with the invention, an improved medication infusion device includes data input pertaining to a current patient condition parameter, such as a current blood glucose reading, and responds thereto to provide an appropriate medication delivery protocol for the patient. This medication delivery protocol can be implemented automatically, recommended via a visual display for convenient acceptance or rejection by the patient, or otherwise overridden in favor of a different or modified medication delivery protocol. Thus, depending upon subjective factors such as current patient activity, eating schedules, etc., the parameter-responsive protocol can be accepted or modified to best suit the individual patient.

In one preferred form, the medication infusion device comprises a compact programmable medication infusion pump adapted to receive and support a syringe carrying a prescribed medication such as insulin. The infusion pump has manual control switches or buttons which can be operated in association with a visual display to program a pump controller for delivering the medication to the patient in accordance with a predetermined dispensing protocol. The pump further includes a sensor or meter for detecting or receiving a current patient parameter, such as a blood glucose reading. The parameter sensor or meter provides a data input to the pump controller for altering the medication delivery protocol in an appropriate manner. In accordance with the invention, the altered protocol can be automatically implemented, but may in the alternative be recommended to the patient by means of the visual display for convenient acceptance or rejection by manipulation of one or more of the control buttons, or otherwise overridden entirely by the patient in favor of a different or modified delivery protocol.

In an alternative form of the invention, the medication infusion device comprises a manually operated syringe-type implement, such as a medication delivery pen of the general type described in European Patent Publication 0,554,995. The delivery pen includes a manually adjustable dial or the like for retracting a syringe plunger through a predetermined stroke, in association with a visual display which indicates the medication dosage to be delivered upon subsequent plunger advancement. The delivery pen includes a controller which receives a patient parameter input from a sensor or meter, such as a current blood glucose reading. The controller responds to the data input representing the patient parameter to recommend a dispensing protocol which can be accepted or modified by the patient.

In a further alternative form of the invention, the sensor or meter may be provided for substantially continuous in vivo patient monitoring, such as an implanted or subcutaneous glucose sensor. The in vivo sensor is associated with a radio telemetry transmitter for sending a patient parameter signal to the infusion device which includes a receiver. The controller of the infusion device responds to the telemetered data input to recommend a medication delivery protocol which can be followed or modified by the patient.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
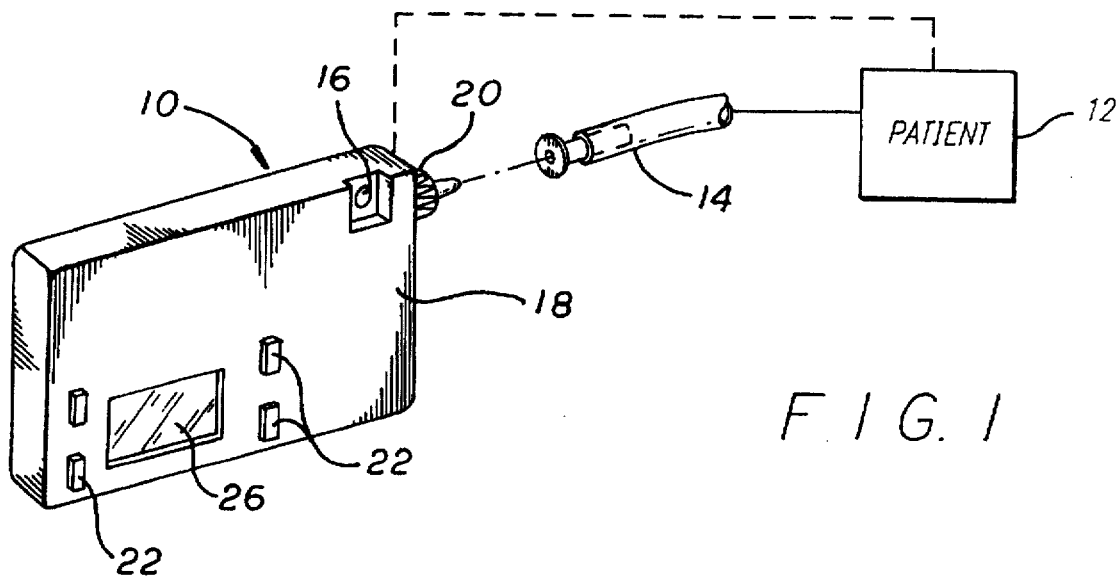
FIG. 1 is an exploded perspective view, shown somewhat in schematic form, illustrating a medication infusion pump with patient parameter data input, in accordance with the novel features of the invention.

As shown in the exemplary drawings, a medication infusion device such as a programmable infusion pump is referred to generally in FIG. 1 by the reference numeral 10. The pump 10 is designed for programmable delivery of a selected medication such as insulin to a patient 12 via a length of infusion tubing 14 and a suitable catheter (not shown). The illustrative pump 10 includes a glucose sensor or meter 16 for receiving and/or deriving an indication of current blood glucose level so that a medication delivery protocol can be modified, as desired.

Figure 2:
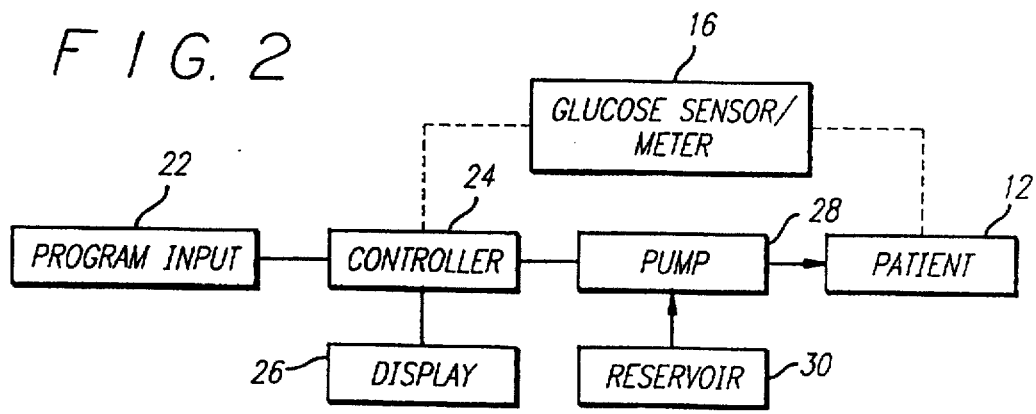
FIG. 2 is a block diagram illustrating operation of the infusion pump of FIG. 1.

The infusion pump 10 shown in FIG. 1 has an overall construction and operation which is generally known in the art. More specifically, the infusion pump 10 comprises a relatively compact pump case or housing 18 adapted to receive and support a syringe (not shown) charged with a selected medication, such as insulin, to be administered to a patient. The medication-containing syringe carries a luer fitting 20 which protrudes outwardly from one side of the pump housing 18 for suitable connection to the infusion tubing 14 through which the medication is delivered to the patient 12. The pump includes an externally exposed array of actuator key switches or buttons 22 for use in operating and/or programming an internal pump controller 24 (FIG. 2). A visual display 26 is provided on the face of the pump housing 18 for displaying information regarding pump programming and/or pump operation. Infusion pumps of this general type are depicted in U.S. Pat. Nos. 4,562,751; 4,678,408; and 4,685,903; which are incorporated by reference herein.

In accordance with one aspect of the invention, the pump controller 24 responds to a data input from the glucose sensor or meter 16, in addition to manually inputted instructions by means of the buttons 22. The glucose sensor or meter 16 is conveniently mounted directly onto the pump housing 18 in a readily accessible position, depending upon the type of glucose sensor or meter used. In one form, a sensor adapted for receiving and reading a glucose test strip can be incorporated into the pump 10, such as a built-in sensor of the type generally available from Miles Inc., of Elkhart, Ind., under the name Glucometer. Alternately, the sensor or meter 16 may be coupled in a suitable manner to an implantable or subcutaneous glucose sensor of the type described, for example, in U.S. Pat. Nos. 4,650,547; 4,671,288; 4,781,798; 4,703,745; and 4,890,620. In either case, data input is provided to the controller 24, as depicted in FIG. 2, so that pump operation may be regulated in accordance with controller programming and in response to a current patient condition parameter such as blood glucose level.

Figure 3:
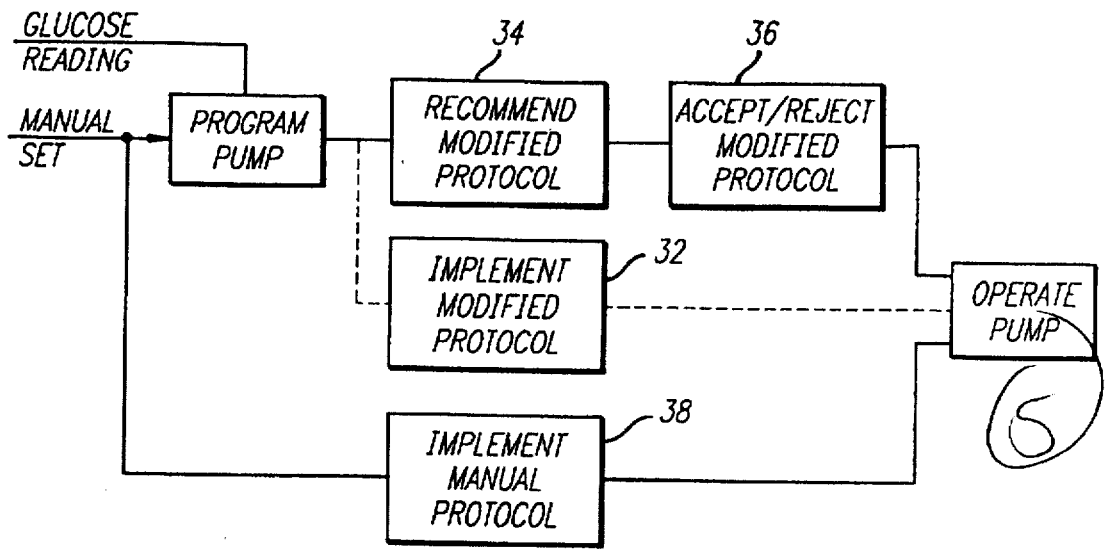
FIG. 3 is a flow chart illustrating operation of the pump controller and recommended dispensing protocol in response to a current patient parameter.

With reference to FIGS. 2 and 3, the controller 24 responds to manipulation of the buttons 22 in addition to the glucose reading data input to operate a pump element 28 which delivers the medication to the patient 12 from a storage reservoir 30, such as a syringe carried by the housing 18. Pursuant to one primary aspect of the present invention, the controller 24 functions in combination with the display 26 and the buttons 22 to provide the patient with important alternatives before actual medication delivery.

More specifically, as shown in the flow chart of FIG. 3, the controller 24 responds to the initial programming and the glucose reading to provide the patient with one of three different protocol alternatives. In one mode of operation, the controller 24 can be set to operate the pump element 28 automatically, by implementing any dispensing protocol modification which is recommended by the controller software, in response to the glucose reading data input. Such automatic implementation of a modified dispensing protocol is depicted by block 32 in FIG. 3.

As one import alternative, the controller software can be set to provide a recommended dispensing protocol which can be visually displayed to the patient by means of the display 26. This recommended protocol step is illustrated in FIG. 3 by block 34. In this flow path, the patient 12 has an opportunity to accept or reject the recommended modified protocol by appropriate manipulation of the buttons 22, as represented by block 36 in FIG. 3. Upon acceptance of the recommended modified protocol, the controller 24 operates the pump the deliver medication in accordance therewith. Upon rejection of the recommended protocol, the controller 24 will deliver medication in accordance with a preset or default protocol previously programmed into the controller 24.

As a further alternative, the controller software can regulate controller operation to permit patient implementation of a modified manually inputted protocol, as indicated by block 38 in FIG. 3. Such implementation of a modified manually inputted protocol would normally occur after rejection of the proposed modified protocol, per block 36, so that the precise dosage and/or timing thereof can be varied according to actual patient activity, eating schedules, etc.

Accordingly, the present invention provides the patient with a high degree of flexibility in adapting and/or modifying a medication dispensing protocol as a function of current glucose blood level readings. The dispensing protocol can be adjusted to reflect current patient activity and other subjective considerations, whereby the actual dosage and timing of such dosages can be uniquely tailored to suit the needs of an individual patient.

Figure 4:
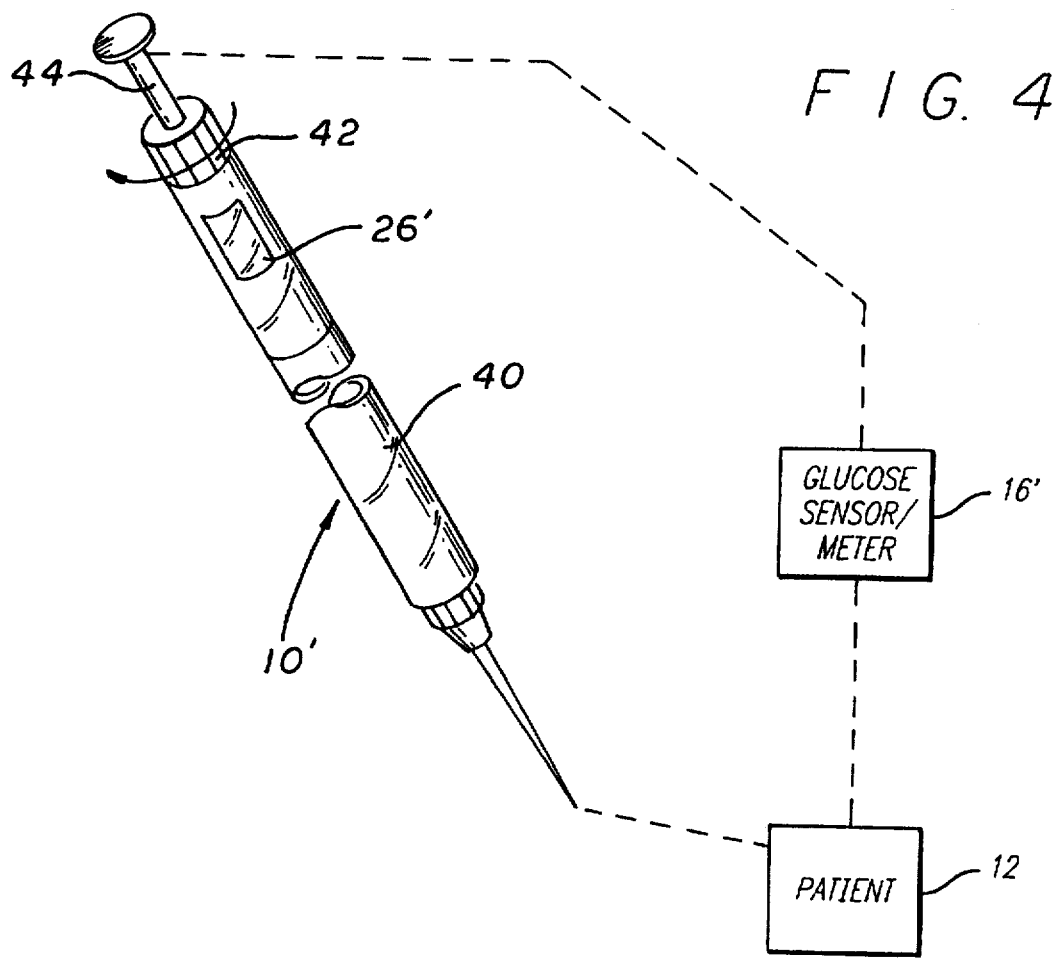
FIG. 4 is an exploded perspective view, shown somewhat in schematic form, depicting one alternative preferred form of the invention.

FIG. 4 shows an alternative form of a medication infusion device which can be operated in accordance with the present invention. As shown, the infusion device comprises a medication delivery pen 10' of the general type disclosed in European Patent Publication 0,554,995, which is incorporated by reference herein. The pen comprises a barrel 40 of generally cylindrical shape for receiving a cartridge (not shown) charged with a selected medication such as insulin for a diabetic. A dial or knob 42 on the aft end of the pen is rotatable to mechanically retract a plunger 44 a preselected distance so that a dial-in medication dosage can be administered to a patient upon subsequent manual plunger depression. A display 26' on the pen barrel 40 displays the dosage to be administered (typically in units), as the dial 42 is rotated. A glucose sensor or meter 16' of the type previously described, such as a built-in sensor for receiving and reading a glucose test strip, provides a data input to the delivery pen 10'. An internal controller (not shown in FIG. 4) responds to the data input to provide a recommended medication dispensing protocol via the display 26'. As previously discussed, the patient may operate the dial 42 and plunger 44 to deliver the recommended dosage, or a modified dosage in accordance with current patient activity and requirements. The internal controller may store a record of actual dispensing events, for subsequent downloading and/or visual display.

Figure 5:
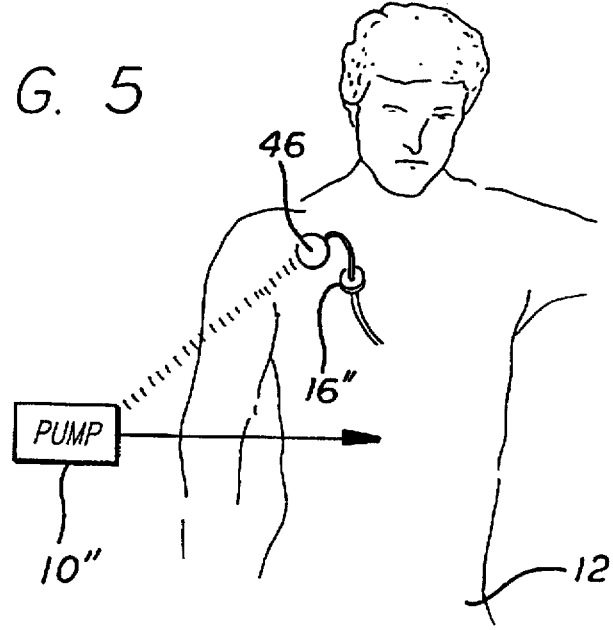
FIG. 5 illustrates, somewhat in schematic form, a further modified arrangement of the invention.

FIG. 5 shows another alternative form of the invention, wherein an in vivo glucose sensor 16" is shown implanted within the body of a patient to provide continuous glucose level readings or readings which may otherwise be taken whenever needed. Alternately, a subcutaneous sensor may be used. An implanted sensor may be constructed in accordance with copending U.S. Ser. No. 231,800, whereas a subcutaneous sensor and related sensor inseration set may be constructed generally in accordance with U.S. Pat. No. 5,390,671, both of which are incorporated by reference herein. The sensor 16" is associated with a transmitter 46 used to send an appropriate glucose data signal via radio telemetry or infrared transmission to an appropriate receiver provided as part of the medication infusion device 10", which may be constructed generally in accordance with the pump 10 shown in FIG. 1. In this system arrangement, the radio telemetered glucose data signal is inputted to the pump 10", which then operates a pump controller (not shown) in accordance with the protocol flow paths described previously with respect to FIG. 3.

A variety of further modifications and improvements to the medication infusion device of the present invention will be apparent to those skilled in the art. Accordingly, no limitation on the invention is intended by way of the foregoing description and accompanying drawings, except as set forth in the appended claims.

What is claimed is:

1. A medication infusion device, comprising:
   reservoir means for receiving and storing a supply of a selected medication;
   delivery means for delivering a selected dosage of the medication from said reservoir means to a patient;
   controller means for automatically controlling said delivery means to deliver the selected medication dosage to the patient according to a first medication dispensing protocol; and
   means for inputting flood data to said controller means, said data being representative of a current patient condition parameter, said controller means including means responsive to said data for recommending a second medication dispensing protocol;
   said controller means including patient accessible manual set means for enabling said controller means to deliver the medication to the patient according to a selected one of said first and second medication dispensing protocols.

2. The medication infusion device of claim 1 further including display means for displaying information pertaining to said selected one of said first and second medication dispensing protocols.

3. The medication infusion device of claim 1 wherein the patient condition parameter comprises a current blood glucose reading.

4. The medication infusion device of claim 3 wherein said device includes a housing having said reservoir means and said delivery means and said controller means mounted therein, said means for inputting data comprising a blood glucose sensor mounted on said housing.

5. The medication infusion device of claim 3 wherein said device includes a housing having said reservoir means and said delivery means and said controller means mounted therein, said means for inputting data comprising an in vivo sensor mounted on the patient and communicatively coupled to said controller means.

6. The medication infusion device of claim 5 wherein said in vivo sensor comprises an implanted sensor.

7. The medication infusion device of claim 5 wherein said in vivo sensor comprises a subcutaneous sensor.

8. The medication infusion device of claim 5 wherein said in vivo sensor is coupled to said controller means by telemetry.

9. The medication infusion device of claim 1 wherein said manual set means is further operable for enabling said controller means to deliver the medication according to a third manually inputted medication dispensing protocol.

10. A medication infusion device, comprising:
    a housing having reservoir means for receiving and storing a supply of a selected medication;
    delivery means on said housing for delivering a selected dosage of the medication from said reservoir means to a patient;
    controller means for recommending one of a plurality of different medication dispensing protocols;
    means for inputting flood data to said controller means, said data being representative of a current patient condition parameter, said controller means responding to said data to select the medication dispensing protocol to be recommended; and
    display means on said housing for displaying the recommended medication dispensing protocol;
    said delivery means being automatically operated by said controller means to deliver the selected medication dosage to the patient, said controller means being programmable for operating said delivery means according to a first medication dispensing protocol, said controller means being responsive to said data to recommend a second medication dispensing protocol, said controller means including patient accessible manual set means for enabling said controller means to deliver the medication to the patient according to a selected one of said first and second medication dispensing protocols.

11. The medication infusion device of claim 10, wherein said manual set means is further operable for enabling said controller means to deliver the medication according to a third manually inputted medication dispensing protocol.

12. The medication infusion device of claim 10 wherein said delivery means is manually operated by the patient.

13. The medication infusion device of claim 10 further including display means for displaying information pertaining to said medication dispensing protocol.

14. The medication infusion device of claim 13 wherein said means for inputting data comprising a blood glucose sensor mounted on said housing.

15. The medication infusion device of claim 13 wherein said means for inputting data comprises an in vivo sensor mounted on the patient and communicatively coupled to said controller means.

16. The medication infusion device of claim 15 wherein said in vivo sensor comprises an implanted sensor.

17. The medication infusion device of claim 15 wherein said in vivo sensor comprises a subcutaneous sensor.

18. The medication infusion device of claim 15 wherein said in vivo sensor is coupled to said controller means by telemetry.

19. In a medication infusion device having a reservoir for receiving and storing a supply of a selected medication, and delivery means for delivering medication from the reservoir to a patient, a method of operating said infusion device comprising the steps of:

- automatically operating the delivery means to deliver a selected dosage of the medication to a patient according to a first medication dispensing protocol;
- inputting flood data representative of a current patient condition parameter to a controller having a plurality of different medication dispensing protocols programmed therein;
- responding to the inputted data to recommend a second medication dispensing protocol from the plurality programmed into the controller; and
- operating the delivery means with patient accessible manual set means to deliver medication to the patient according to one of the first and second medication dispensing protocols or a different dispensing protocol.

20. The method of claim 19 further including displaying the recommended dispensing protocol.

21. The method of claim 19 wherein the patient condition parameter comprises a current blood glucose reading.

* * * * *

UNITED STATES PATENT AND TRADEMARK OFFICE
CERTIFICATE OF CORRECTION

PATENT NO.   : 5,665,065
DATED        : September 9, 1997
INVENTOR(S)  : Fredric C. Colman and Peter C. Lord It is certified that error appears in the above-identified patent and that said Letters Patent is hereby corrected as shown below:

In claim 1, col. 6, line 11, delete "flood" and insert --blood--.

In claim 10, col. 6, line 59, delete "flood" and insert --blood--.

In claim 19, col. 8, line 12, delete "flood" and insert --blood--.

Signed and Sealed this

Sixth Day of January, 1998

Attest:

BRUCE LEHMAN

Attesting Officer    Commissioner of Patents and Trademarks